United States Patent
Steiner et al.

(10) Patent No.: US 8,671,937 B2
(45) Date of Patent: Mar. 18, 2014

(54) UNIT DOSE CAPSULES AND DRY POWDER INHALER

(75) Inventors: Solomon S. Steiner, Mount Kisco, NY (US); Per B. Fog, Bedford Hills, NY (US); Trent Poole, South Amherst, MA (US); Robert Feldstein, Yonkers, NY (US)

(73) Assignee: Mannkind Corporation, Valencia, CA (US)

( * ) Notice: Subject to any disclaimer, the term of this patent is extended or adjusted under 35 U.S.C. 154(b) by 0 days.

(21) Appl. No.: 13/421,529

(22) Filed: Mar. 15, 2012

(65) Prior Publication Data

US 2012/0174923 A1    Jul. 12, 2012

Related U.S. Application Data

(63) Continuation of application No. 11/934,643, filed on Nov. 2, 2007, now Pat. No. 8,156,936, which is a continuation of application No. 09/621,092, filed on Jul. 21, 2000, now Pat. No. 7,305,986.

(60) Provisional application No. 60/145,464, filed on Jul. 23, 1999, provisional application No. 60/206,123, filed on May 22, 2000.

(51) Int. Cl.
*A61M 11/00* (2006.01)

(52) U.S. Cl.
USPC ............................... 128/203.15; 128/203.12

(58) Field of Classification Search
USPC ............ 128/203.15, 203.12, 203.19; 604/58; 424/453, 454, 458, 467
See application file for complete search history.

(56) References Cited

U.S. PATENT DOCUMENTS

| | | | |
|---|---|---|---|
| 2,549,303 A | 4/1951 | Friden | |
| 3,337,740 A | 8/1967 | Gray et al. | |
| 3,518,340 A | 6/1970 | Raper | |
| 3,622,053 A | 11/1971 | Ryden | |
| 3,669,113 A | 6/1972 | Altounyan et al. | |
| 3,823,816 A | 7/1974 | Controulis | |
| 3,823,843 A | 7/1974 | Stephens et al. | |
| 3,856,142 A | 12/1974 | Vessalo | |
| 3,906,950 A | 9/1975 | Cocozza | |
| 3,921,637 A | 11/1975 | Bennie et al. | |
| 4,040,536 A | 8/1977 | Schwarz | |
| 4,047,525 A | 9/1977 | Kulessa et al. | |
| 4,148,308 A | 4/1979 | Sayer | |
| 4,206,758 A | 6/1980 | Hallworth et al. | |
| 4,210,140 A | 7/1980 | James et al. | |
| 4,268,460 A | 5/1981 | Boiarski et al. | |
| 4,275,820 A | 6/1981 | LeBlond | |
| 4,300,546 A | 11/1981 | Kruber | |
| 4,407,525 A | 10/1983 | Hoppe | |
| 4,456,007 A | 6/1984 | Nakao et al. | |
| 4,487,327 A | 12/1984 | Grayson | |
| 4,524,769 A | 6/1985 | Wetterlin | |
| 4,534,345 A | 8/1985 | Wetterlin | |

(Continued)

FOREIGN PATENT DOCUMENTS

DE    3639836    6/1988
DE    19519840    12/1996

(Continued)

*Primary Examiner* — Steven Douglas
(74) *Attorney, Agent, or Firm* — K&L Gates LLP; Louis C. Cullman; Hal Gibson

(57) ABSTRACT

Described is a dry powder inhaler comprising an intake section; a mixing section, and a mouthpiece.

13 Claims, 10 Drawing Sheets

(56) References Cited

U.S. PATENT DOCUMENTS

| | | | |
|---|---|---|---|
| 4,592,348 | A | 6/1986 | Waters, IV et al. |
| 4,792,451 | A | 12/1988 | Kim |
| 4,841,964 | A | 6/1989 | Hurka et al. |
| 4,907,583 | A | 3/1990 | Wetterlin et al. |
| 4,926,852 | A | 5/1990 | Zoltan et al. |
| 4,991,605 | A | 2/1991 | Keritsis |
| 5,027,806 | A | 7/1991 | Zoltan et al. |
| 5,067,500 | A | 11/1991 | Keritsis |
| 5,152,284 | A | 10/1992 | Valentini et al. |
| 5,170,801 | A | 12/1992 | Casper et al. |
| 5,239,992 | A | 8/1993 | Bougamont et al. |
| 5,301,666 | A | 4/1994 | Lerk et al. |
| 5,327,883 | A | 7/1994 | Williams et al. |
| 5,328,464 | A | 7/1994 | Kriesel et al. |
| 5,337,740 | A | 8/1994 | Armstrong et al. |
| 5,404,871 | A | 4/1995 | Goodman et al. |
| 5,447,151 | A | 9/1995 | Bruna et al. |
| 5,476,093 | A | 12/1995 | Laniken |
| 5,483,954 | A | 1/1996 | Mecikalski |
| 5,487,378 | A | 1/1996 | Robertson et al. |
| 5,492,112 | A | 2/1996 | Mecikalski et al. |
| 5,503,144 | A | 4/1996 | Bacon |
| 5,505,194 | A | 4/1996 | Adjei et al. |
| 5,524,613 | A | 6/1996 | Haber et al. |
| 5,542,411 | A | 8/1996 | Rex |
| 5,562,918 | A | 10/1996 | Stimpson |
| 5,568,884 | A | 10/1996 | Bruna |
| 5,577,497 | A | 11/1996 | Mecikalski et al. |
| 5,622,166 | A | 4/1997 | Eisele et al. |
| 5,632,971 | A | 5/1997 | Yang |
| 5,645,051 | A | 7/1997 | Schultz et al. |
| 5,655,523 | A | 8/1997 | Hodson et al. |
| 5,687,710 | A | 11/1997 | Ambrosio et al. |
| 5,699,789 | A | 12/1997 | Hendricks |
| 5,714,007 | A | 2/1998 | Pletcher et al. |
| 5,727,546 | A | 3/1998 | Clarke et al. |
| 5,740,794 | A | 4/1998 | Smith et al. |
| 5,746,197 | A | 5/1998 | Williams |
| 5,752,505 | A | 5/1998 | Ohki et al. |
| 5,755,218 | A | 5/1998 | Johansson et al. |
| 5,758,638 | A | 6/1998 | Kreamer |
| 5,775,320 | A | 7/1998 | Patton et al. |
| 5,785,049 | A | 7/1998 | Smith et al. |
| 5,797,391 | A | 8/1998 | Cook et al. |
| 5,813,397 | A | 9/1998 | Goodman et al. |
| 5,881,719 | A | 3/1999 | Gottenauer et al. |
| 5,884,620 | A | 3/1999 | Gonda et al. |
| 5,896,855 | A | 4/1999 | Hobbs et al. |
| 5,901,703 | A | 5/1999 | Ohki et al. |
| 5,904,139 | A | 5/1999 | Hauser |
| 5,921,237 | A | 7/1999 | Eisele et al. |
| 5,983,893 | A | 11/1999 | Wetterlin |
| 6,006,747 | A | 12/1999 | Eisele et al. |
| 6,029,663 | A | 2/2000 | Eisele et al. |
| 6,055,980 | A | 5/2000 | Mecikalski et al. |
| 6,073,629 | A | 6/2000 | Hardy et al. |
| 6,109,261 | A | 8/2000 | Clarke et al. |
| 6,116,237 | A | 9/2000 | Schultz et al. |
| 6,116,238 | A | 9/2000 | Jackson et al. |
| 6,116,239 | A | 9/2000 | Volgyesi |
| 6,158,431 | A | 12/2000 | Poole |
| 6,273,085 | B1 | 8/2001 | Eisele et al. |
| 6,273,086 | B1 | 8/2001 | Ohki et al. |
| 6,298,846 | B1 | 10/2001 | Ohki et al. |
| 6,328,034 | B1 | 12/2001 | Eisele et al. |
| 6,347,629 | B1 | 2/2002 | Braithwaite |
| 6,363,932 | B1 | 4/2002 | Forchione et al. |
| 6,394,085 | B1 | 5/2002 | Hardy et al. |
| 6,418,926 | B1 | 7/2002 | Chawla |
| 6,427,688 | B1 | 8/2002 | Ligotke et al. |
| 6,470,884 | B2 | 10/2002 | Horlin |
| 6,543,448 | B1 | 4/2003 | Burr et al. |
| 6,546,929 | B2 | 4/2003 | Burr et al. |
| 6,561,186 | B2 | 5/2003 | Casper et al. |
| 6,575,160 | B1 | 6/2003 | Volgyesi |
| 6,578,571 | B1 | 6/2003 | Watt |
| 6,606,992 | B1 | 8/2003 | Schuler et al. |
| 6,644,309 | B2 | 11/2003 | Casper et al. |
| 6,655,379 | B2 | 12/2003 | Clark et al. |
| 6,655,381 | B2 | 12/2003 | Keane et al. |
| 6,681,767 | B1 | 1/2004 | Patton et al. |
| 6,698,421 | B2 | 3/2004 | Attolini |
| 7,305,986 | B1 | 12/2007 | Steiner et al. |
| 7,464,706 | B2 | 12/2008 | Steiner et al. |
| 8,146,588 | B2 | 4/2012 | Steiner et al. |
| 8,156,936 | B2 | 4/2012 | Steiner et al. |
| 8,215,300 | B2 | 7/2012 | Steiner et al. |
| 2002/0053347 | A1 | 5/2002 | Ziaee |
| 2004/0182387 | A1 | 9/2004 | Steiner et al. |
| 2005/0252508 | A1 | 11/2005 | Koerner |
| 2006/0239934 | A1 | 10/2006 | Cheatham et al. |
| 2006/0243275 | A1 | 11/2006 | Ruckdeschel et al. |
| 2009/0241949 | A1 | 10/2009 | Smutney |
| 2012/0192865 | A1 | 8/2012 | Steiner |
| 2012/0240929 | A1 | 9/2012 | Steiner |

FOREIGN PATENT DOCUMENTS

| | | | |
|---|---|---|---|
| EP | 143524 | | 6/1985 |
| EP | 180543 | | 5/1986 |
| EP | 308637 | | 3/1989 |
| EP | 388621 | | 9/1990 |
| EP | 581473 | | 2/1994 |
| EP | 666085 | | 8/1995 |
| EP | 844007 | | 12/1998 |
| EP | 640354 | B1 | 12/2001 |
| EP | 1923087 | | 5/2008 |
| GB | 716815 | | 10/1954 |
| GB | 2072536 | | 10/1981 |
| GB | 2148841 | | 6/1985 |
| GB | 2253200 | A | 9/1992 |
| GB | 2262452 | | 6/1993 |
| JP | 10234827 | | 9/1998 |
| WO | 91/19524 | | 12/1991 |
| WO | 9208509 | | 5/1992 |
| WO | 94/19041 | | 9/1994 |
| WO | 9505208 | | 2/1995 |
| WO | 96/22802 | | 8/1996 |
| WO | 97/01365 | | 1/1997 |
| WO | 98/26827 | | 6/1998 |
| WO | 98/41255 | | 9/1998 |
| WO | 01/07107 | | 2/2001 |
| WO | 01/66064 | | 9/2001 |
| WO | 03/05547 | | 7/2003 |
| WO | 2007/068896 | | 6/2007 |

PISTON NORMALLY CLOSES
INTAKE PORT

2ND SPRING NOT SHOWN

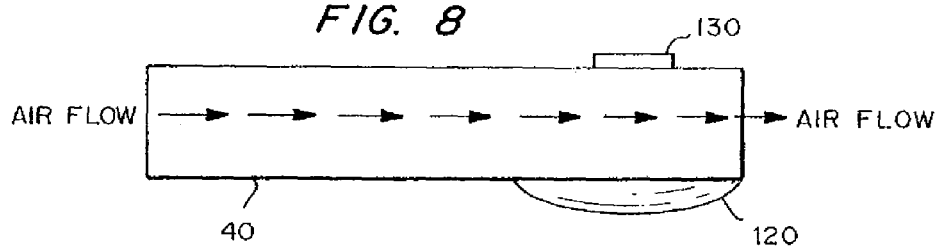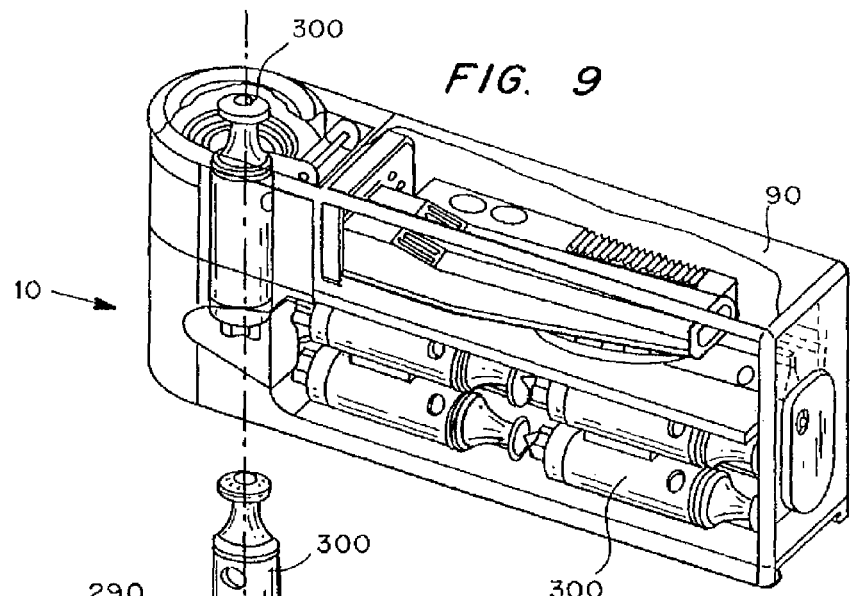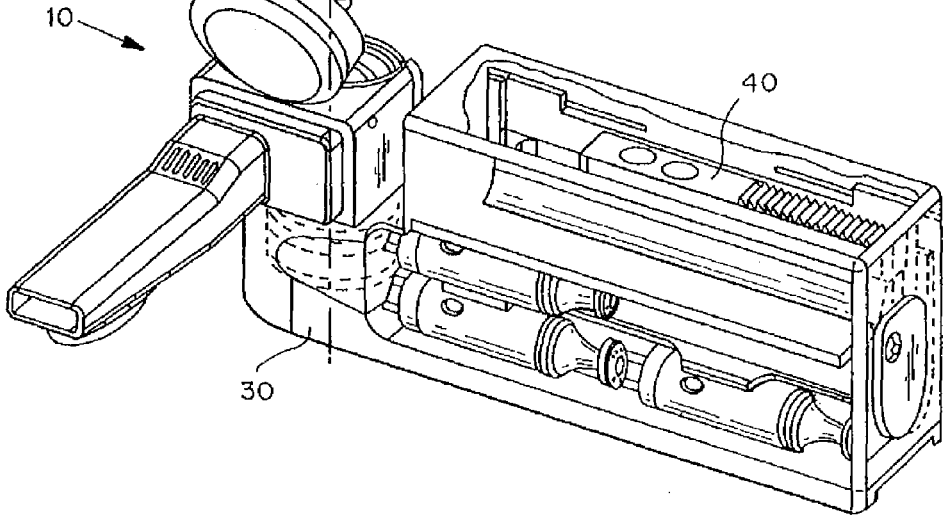

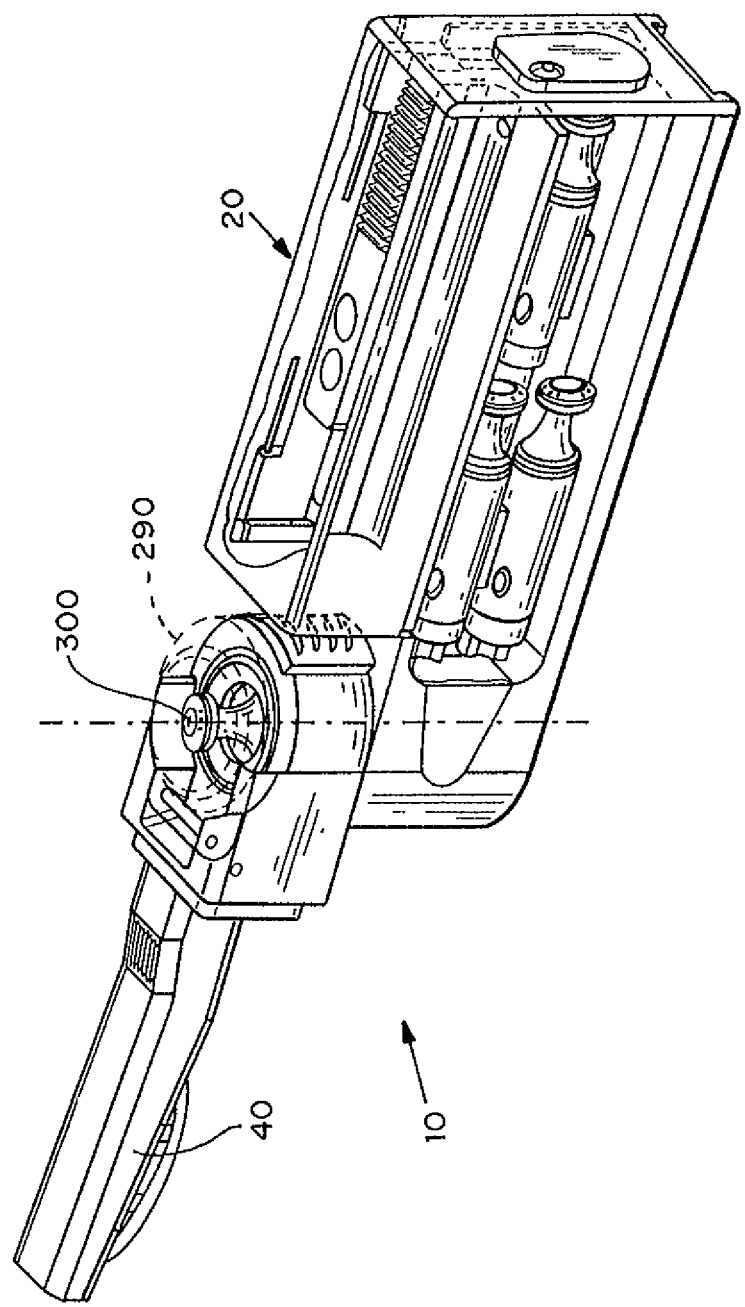

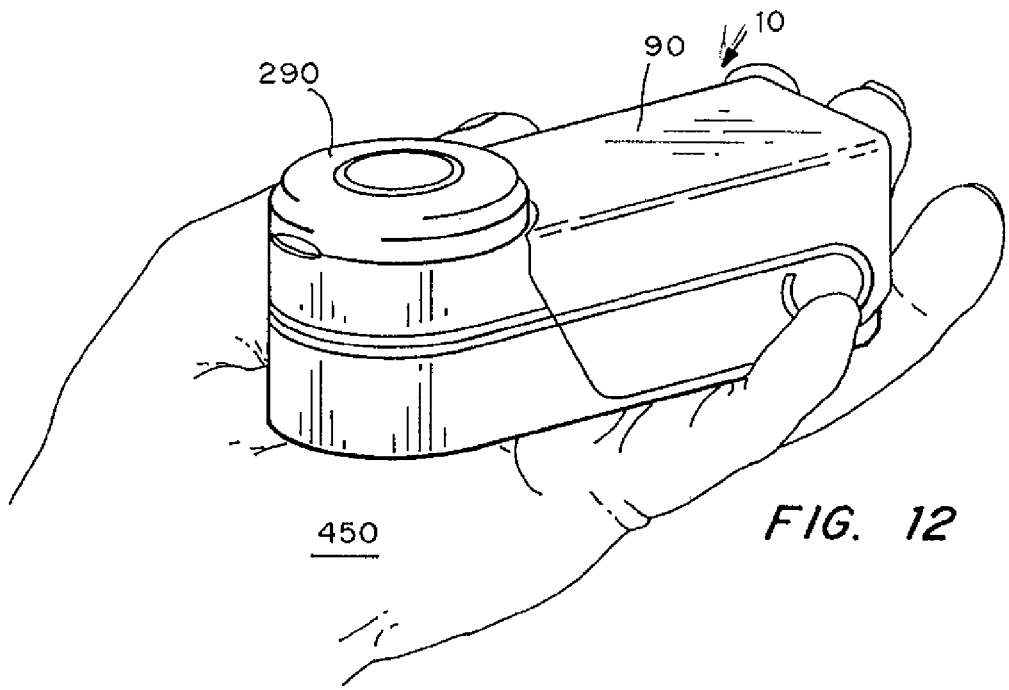
FIG. 12
FIG. 13
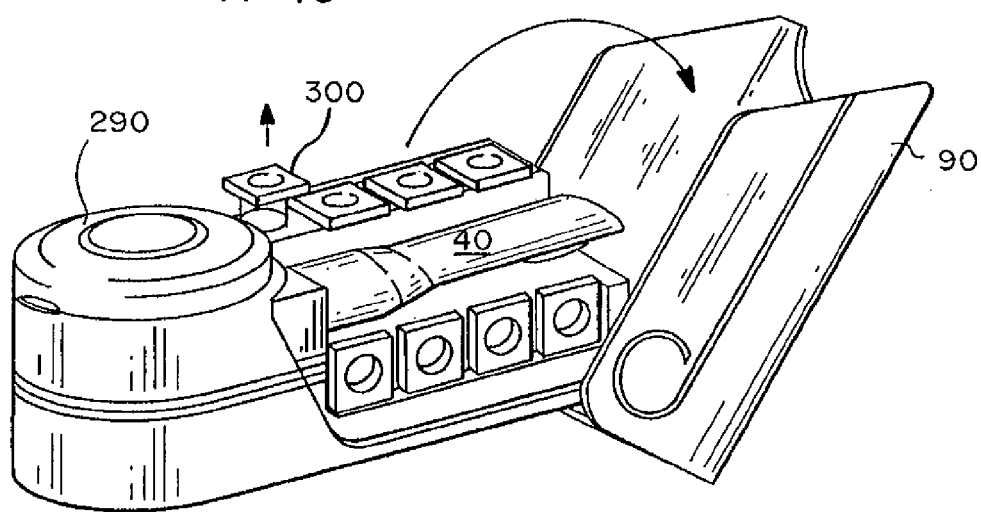

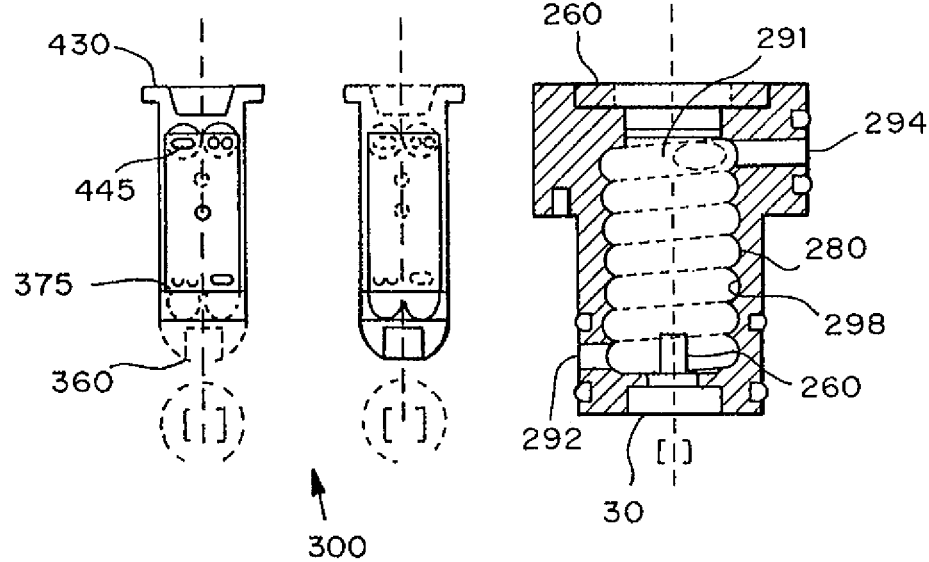
FIG. 18 PARTICLE ENTRAINMENT TURBOCELL MODULE
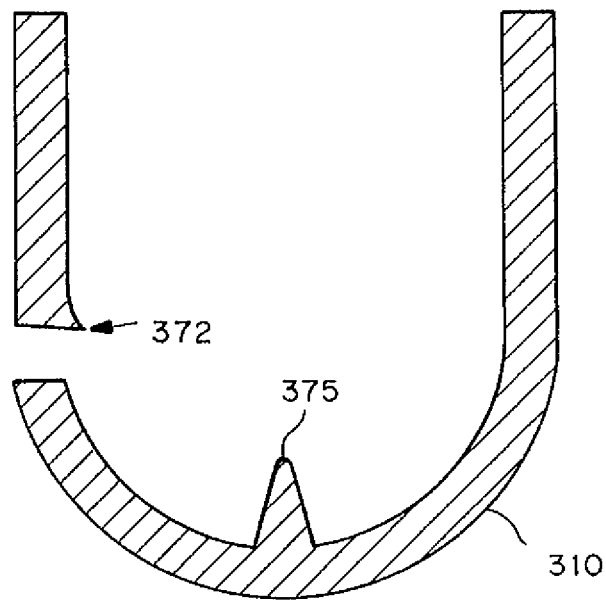
FIG. 19

UNIT DOSE CAPSULES AND DRY POWDER INHALER

CROSS REFERENCE TO RELATED APPLICATIONS

The present application is a continuation of U.S. patent application Ser. No. 11/934,643 filed on Nov. 2, 2007, which is a continuation of U.S. patent application Ser. No. 09/621,092 filed on Jul. 21, 2000, now U.S. Pat. No. 7,305,986, which claims the benefit under 35 U.S.C. §119(e) of U.S. Provisional Patent Application Nos. 60/145,464 filed Jul. 23, 1999 and 60/206,123 filed May 22, 2000, all of which are incorporated by reference herein in their entirety.

FIELD OF THE INVENTION

The present invention is in the field of inhalers.

BACKGROUND OF THE INVENTION

In the early 1970's it was found that certain medicines could be administered in dry-powder form directly to the lungs by inhalation through the mouth or inspiration through the nose. This process allows the medicine to bypass the digestive system, and may, in certain cases, allow smaller does to be used to achieve the same results or orally ingested or injected medicines. In some cases, it provides a delivery technique that reduces side effects for medicines taken by other medicines.

Inhaler devices typically deliver their medicinal in a liquid mist or a powder mist. The liquid mist is typically created by a chlorofluorocarbon propellant. However, with the ban on chlorofluorocarbons by the Montreal protocol, interest has turned to dry powder inhalers.

For a dry powder inhaler to work effectively, it must deliver fine particles of medicinal powder that do not agglomerate, and do not end up striking, and being absorbed by the patient's mouth or upper oropharyngeal region. Air flow must therefore not be too fast. Furthermore, it should not be difficult for a patient to load with medicine or to use with the proper technique. Current dry particle inhalers fail in one or more of these important criteria.

SUMMARY OF THE INVENTION

Described is a dry powder inhaler comprising an intake section; a mixing section, and a mouthpiece. The mouthpiece is connected by a swivel joint to the mixing section, and may swivel back onto the intake section and be enclosed by a cover. The intake chamber comprises a special piston with a tapered piston rod and spring, and one or more bleed-through orifices to modulate the flow of air through the device. The intake chamber further optionally comprises a feedback module to generate a tone indicating to the user when the proper rate of airflow has been achieved. The mixing section holds a capsule with holes containing a dry powder medicament, and the cover only can open when the mouthpiece is at a certain angle to the intake section. The mixing section further opens and closes the capsule when the intake section is at a certain angle to the mouthpiece. The mixing section is a Venturi chamber configured by protrusions or spirals to impart a cyclonic flow to air passing through the mixing chamber. The mouthpiece includes a tongue depressor, and a protrusion to contact the lips of the user to tell the user that the DPI is in the correct position. An optional storage section, with a cover, holds additional capsules. The cover for the mouthpiece, and the cover for the storage section may both be transparent magnifying lenses.

The capsules may be two-part capsules where each portion has apertures which correspond to apertures in the other half when each half is partially fitted to the other half, and fully fitted to the other half. All the apertures may be closed when the two halves are rotated around their longitudinal axes with respect to each other. Each capsule may have a unique key on each half that only fits with a particular inhaler.

Therefore it is an object of the invention to provide a dry particle inhaler that can fold into a compact form.

Therefore it is an object of the invention to provide a dry particle inhaler that can be loaded with medicament easily.

Therefore it is an object of the invention to provide a dry particle inhaler where the small writing on a capsule of medicament can be easily read.

Therefore it is an object of the invention to provide a dry particle inhaler where a capsule containing medicament can only be inserted when a person unfolds the inhaler for use.

Therefore it is an object of the invention to provide a dry particle inhaler where the air flow through the device is regulated.

Therefore it is an object of the invention to provide a dry particle inhaler to provide a means for indicating to the user when the air flow is at the correct rate.

Therefore it is an object of the invention to provide a dry particle inhaler where particles of drug are dispersed finely.

These and other objects of the invention will be readily apparent upon a reading of the present specification, claims and drawings.

BRIEF DESCRIPTION OF THE SEVERAL VIEWS OF THE DRAWINGS

FIG. 8 is a schematic view of the mouthpiece.

FIG. 9 is a perspective view of a specific embodiment of the dry particle inhaler in the closed position, with a capsule inserted into the mixing section, and extra capsules stored in the storage section.

FIG. 10 is a perspective view of a specific embodiment of the dry particle inhaler showing a capsule being loaded in to the mixing section.

FIG. 11 is a perspective view of a specific embodiment of the dry particle inhaler showing a capsule inserted into the mixing section, and the mouthpiece extended for use.

FIGS. 12, 13, 14, and 15 follow each other in temporal sequence.

FIG. 12 is a perspective view of a specific embodiment of the dry particle inhaler showing a closed mouthpiece cover.

FIG. 13 is a perspective view of a specific embodiment of the dry particle inhaler showing an open mouthpiece cover.

FIG. 14 is a perspective view of a specific embodiment of the dry particle inhaler showing an open mouthpiece cover, an open mixing section cover, and a capsule about to be inserted into the mixing section.

FIG. 15 is a perspective view of a specific embodiment of the dry particle inhaler showing the mouthpiece extended for use.

FIG. 18 is a cutaway view of a capsule and a portion of the mixing section.

FIG. 19 is a cutaway view of half of a capsule, showing a cone in the interior and a secondary hole with a chamfered, or beveled, edge.

TABLE OF REFERENCE NUMBERS

- 10 dry powder inhaler device
- 20 intake section
- 30 mixing section
- 40 mouthpiece
- 50 air passage through dry powder inhaler device
- 60 longitudinal axis of intake section
- 70 longitudinal axis of mouthpiece section
- 80 swivel joint connecting mouthpiece and mixing section
- 90 cover for mouthpiece
- 100 protrusions on mouthpiece cover
- 110 depressions on dry particle inhaler cover to mate with protrusions on mouthpiece cover
- 120 tongue depressor on mouthpiece
- 130 protrusion on surface of mouthpiece to contact lips of device user
- 135 opening of mouthpiece to be fitted into user's mouth
- 140 intake port
- 150 flow regulator
- 160 bleed orifice
- 170 piston
- 180 piston head
- 190 piston rod
- 200 proximal portion of piston rod
- 210 distal portion of piston rod
- 220 spring
- 230 inner walls of intake section inner chamber
- 240 feedback module
- 250 mechanical fasteners in storage section
- 260 holder in mixing section for capsule
- 270 Venturi chamber
- 280 spiral shape or protrusions to impart cyclonic flow to air
- 290 cover for mixing chamber
- 291 interior of mixing section
- 292 air flow entrance to mixing section
- 294 air flow exit from mixing section
- 296 latch mechanism for mixing section cover
- 298 interior wall of mixing section
- 300 capsule
- 310 first tube
- 320 open end of first tube
- 330 closed end of first tube
- 340 long axis of first tube
- 350 protrusion on first tube
- 360 keying surface on first tube
- 370 secondary holes in first tube
- 372 chamfered edge of secondary hole
- 375 cone in interior of first tube
- 380 second tube
- 390 open end of second tube
- 400 closed end of second tube
- 410 long axis of second tube
- 420 protrusion on second tube
- 430 keying surface on second tube
- 440 secondary holes in second tube
- 445 cone in interior of second tube
- 450 hand of user
- 460 air flow direction
- 470 storage section
- 480 storage section cover

DETAILED DESCRIPTION OF THE INVENTION

Figure 1:
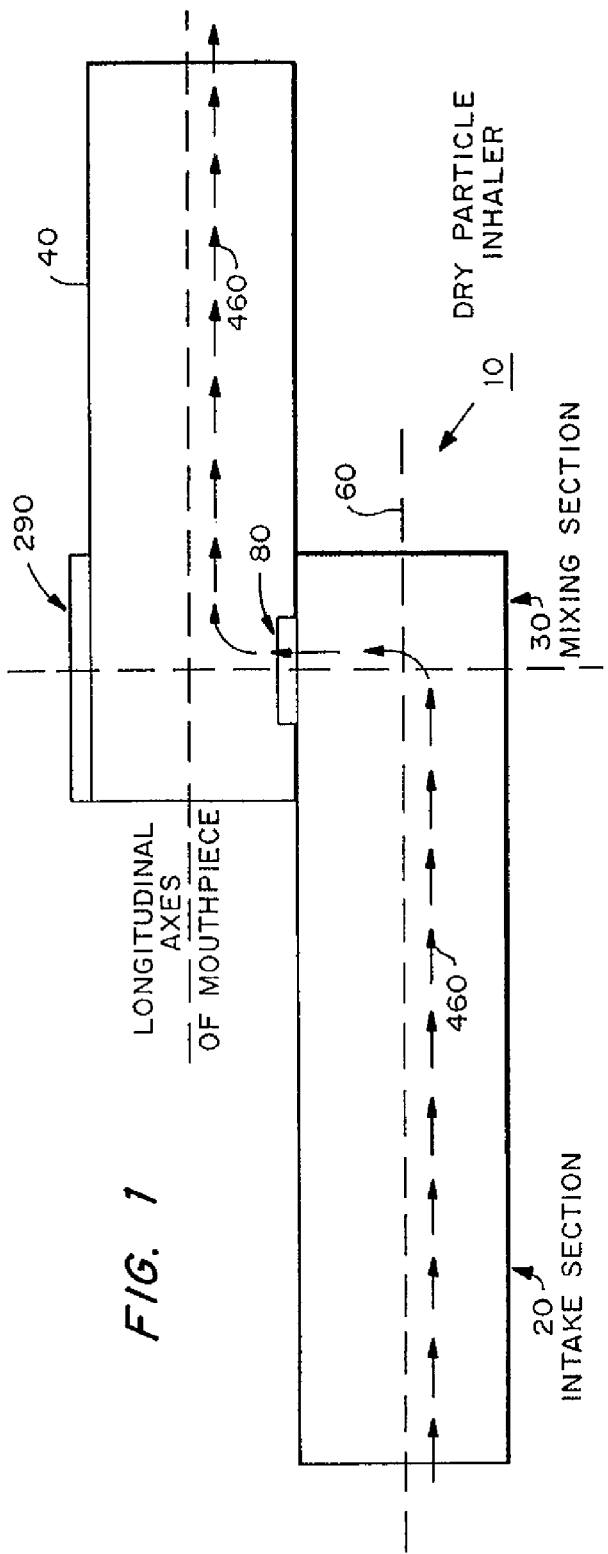
FIG. 1 is a schematic view of the dry particle inhaler described herein.

FIG. 1 is a schematic drawing of the dry powder inhaler (10) described herein. It comprises an intake section (20), a mixing section (30) and a mouthpiece (40). An air passage (50) goes through the intake section (20), a mixing section (30) and a mouthpiece (40). A swivel joint (80) connects the mouthpiece (40) to the mixing section (30). The mixing section (20) has a cover (290) which may be a transparent magnifying lens.

Arrow (460) shows the direction of air flow through the air passage (50) through the dry powder inhaler (10).

Figure 2:
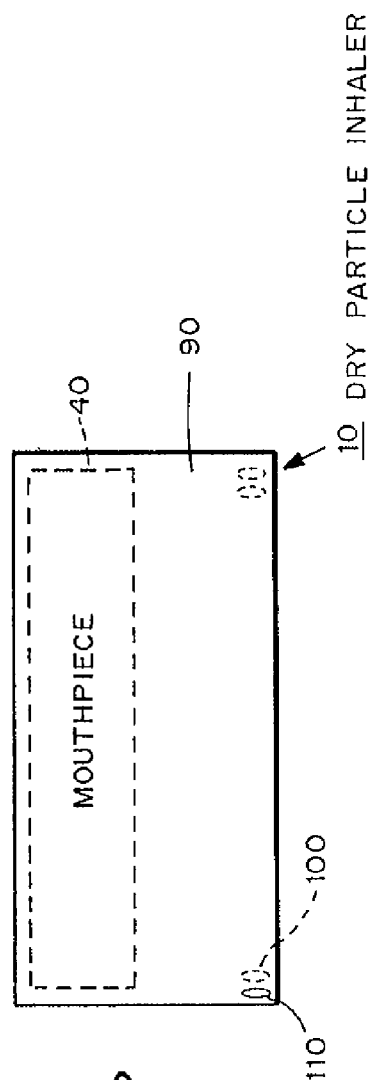
FIG. 2 is schematic view of the mouthpiece cover.

FIG. 2 shows the mouthpiece cover (90) in the closed position over the dry particle inhaler (10). Protrusions (100) on the mouthpiece cover (90) mate with grooves or depressions (110) on the dry particle inhaler (10), to join the mouthpiece cover (90) to the dry particle inhaler (10).

Figure 3:
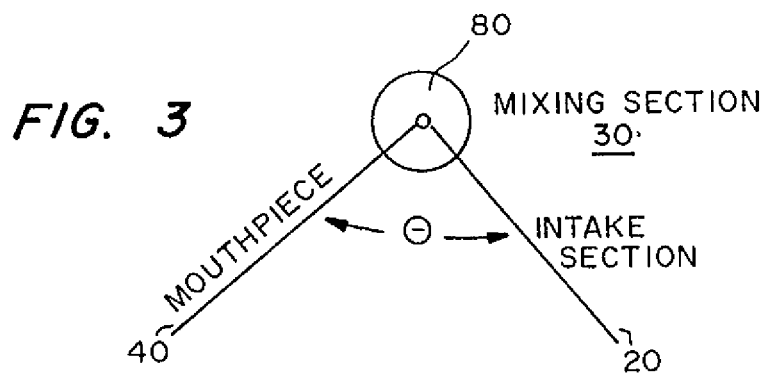
FIG. 3 is schematic view showing the angle between the intake section and the mouthpiece.

FIG. 3 is a schematic of the showing the mouthpiece (40) and the intake section (20) as represented by the longitudinal axis of the mouthpiece (70) and the longitudinal axis of the intake section (60). The swivel joint (80) connecting the mouthpiece (40) to the intake section (20) at the mixing section (30) may be regarded as the vertex of the angle. The importance of the angle (here called theta) between these two longitudinal axes will be further explained.

Figure 4:
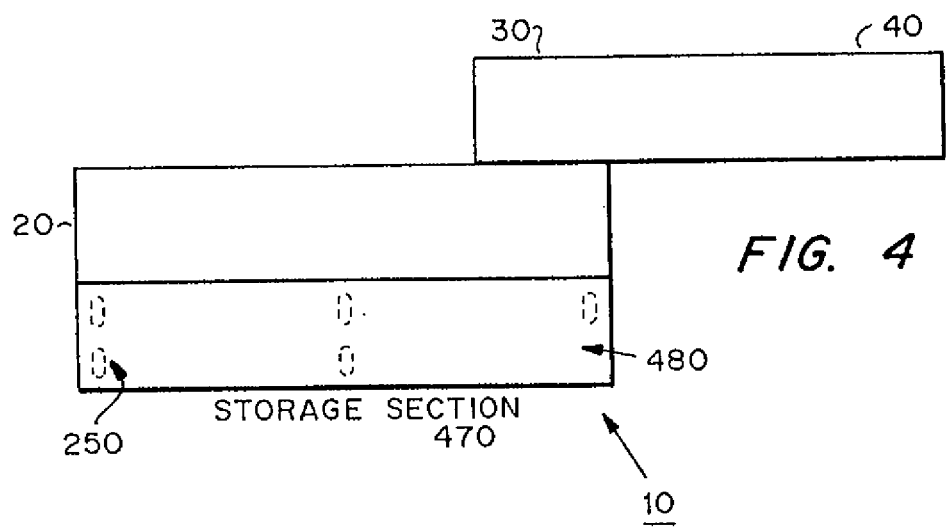
FIG. 4 is a schematic view of the dry particle inhaler, showing the storage section.

FIG. 4 shows the dry particle inhaler (10) with a storage section (470). Indicated as being inside the storage section (470) are mechanical fasteners (250) which operate to hold medicament capsules (300) (not shown in this Figure) in the storage section. In this embodiment, the storage section (470) is shown as appended to the intake section (20). The storage section has a cover (480) which may be a transparent magnifying lens, to allow the user to easily read writing on medicament capsules stored therein. The storage section cover (480) may swivel outward, or slide open on a track (not shown), or open by a variety of mechanisms known to those of skill in the art.

Figure 5:
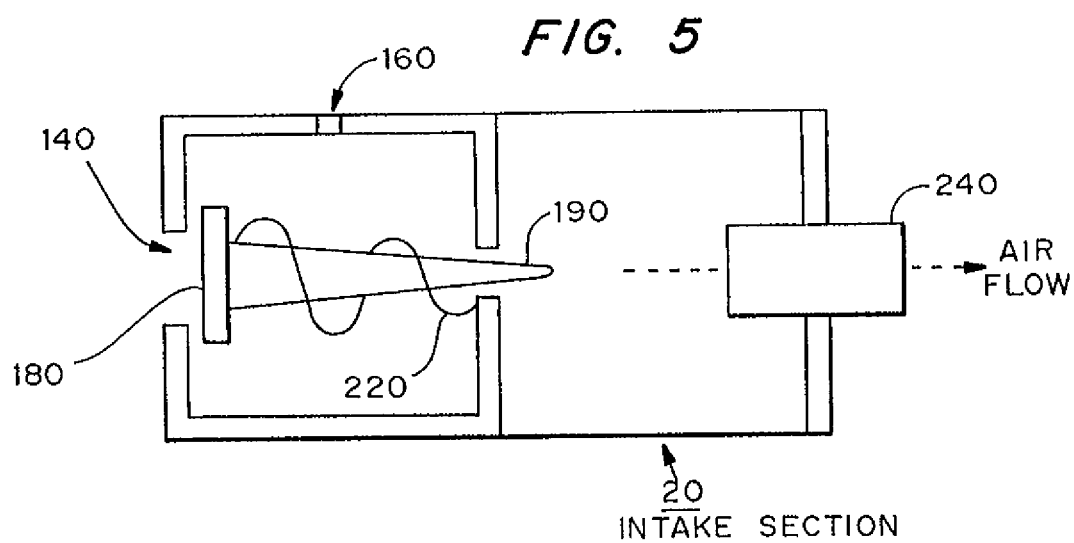
FIG. 5 is a schematic view of the intake section of the dry particle inhaler, showing the flow regulator and the feedback module.

FIG. 5 shows the intake section (20) of the dry particle inhaler (10). The direction of air flow is shown by the arrow (460). Air is admitted through an intake port (140) and one or more bleed orifices (160) [The bleed orifices may also be styled as secondary ambient air intake ports].

The piston (170) normally covers the intake port (140). When the user (not shown) inspires, the piston head (180) is drawn backwards, at a steady rate modulated by the spring (220). The spring (220) is fixed to the piston (170) and the inner wall (230) of the intake section chamber. Thus the rate of air flow is controlled. The air flow is further controlled by the tapering of the piston rod (190), past which the air flows. For further control of the air flow, a second spring (not shown) may also control the rate of movement of the piston (170).

The piston (170) and spring (220) combination allow the user (not shown) to generate a vacuum in his lungs before the intake port (140) opens.

Thus, by the time enough vacuum is generated to open the intake port (140), there will be sufficient air flow at a sufficient rate in the dry particle inhaler (10) to draw most of the medicament in the capsule (not shown) out of the inhaler into the proper place in the lungs of the user.

A feedback module (240) generates a signal to the user (not shown), which tells the user whether he is inspiring at the correct rate. The signal may be an audible one, in one embodiment a tone that is at a steady pitch when air flow is at a certain steady rate. In one embodiment of the dry particle inhaler (10), the signal is generated mechanically, such as be a musical reed. In another embodiment of the invention, the signal might be generated electronically, after electronic measurement of the air flow rate. The feedback module (240) would include a means for increasing or lessening the signal strength, or turning the signal off entirely. If the signal were generated by a reed, the mechanism for turning off the signal might be covering a bleed orifice which might admit the air flow generating the signal. If the signal were generated electronically, a simple push button or dial might turn on and off the signal.

Figure 6:
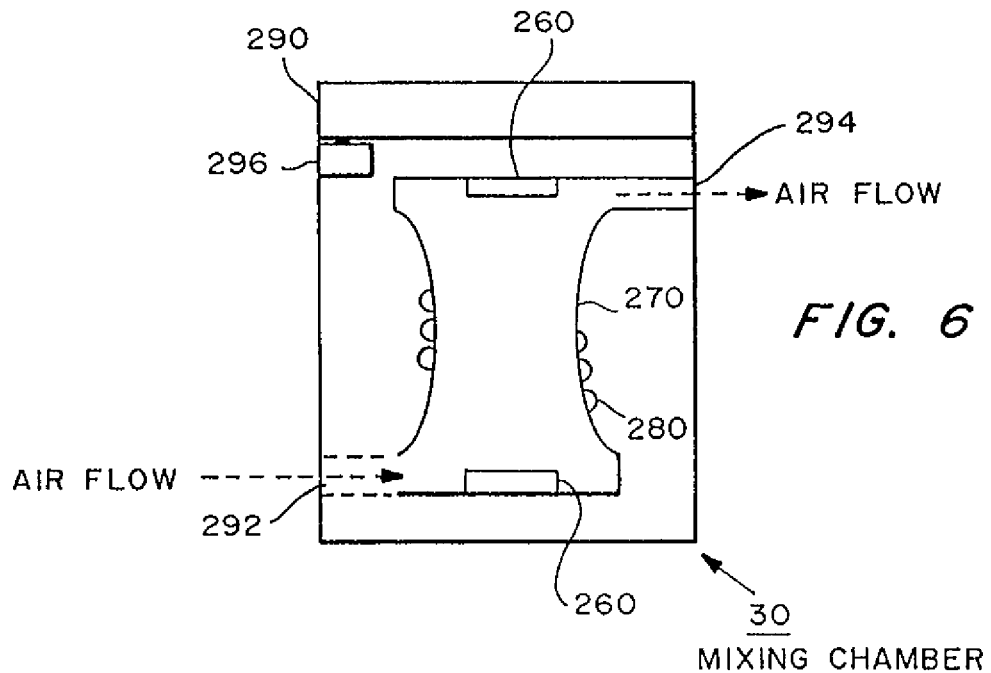
FIG. 6 is a schematic view of the mixing section.

FIG. 6 shows a schematic of the mixing section (30) of the present invention. The mixing section has a cover (290), and a holder (260) for a medicament capsule (not shown). The holder (260) is a mechanism which grips and turns the capsule (not shown) to open and close it as the longitudinal axis (70) of the mouthpiece is rotated about the swivel joint (80) relative to the longitudinal axis (60) of the intake section. Such a mechanism may be straightforward: in a simplest embodiment, both the top and bottom halves (not shown) of the capsule could be fixed to their respective holders (260).

The Venturi chamber (270) speeds the flow of air near the capsule (not shown). Air flows in at (292), and out through (294). In one embodiment, air flows both through and around a capsule (not shown) holding a dry powder medicament. The special shape of the Venturi chamber (270), which further includes protrusions or spiral shapes (280), imparts a cyclonic flow to the air passing through the mixing section (30).

This helps to de-agglomerate particles of dry powder. The spiral shape of the interior of the mixing section (291) can be two separate spirals, in one embodiment of the invention. Mixing section (30) therefore provides the means whereby air flow is speeded up to suspend dry particles in air and de-agglomerate them, and then slow the air flow somewhat while the particles are still suspended in air. The cover (290) for the mixing section (30) may be a transparent magnifying lens, so that any writing on the capsule (not shown) may be read easily.

In one embodiment of the dry particle inhaler (10), the cover (290) of the mixing section may not be opened unless the longitudinal axis (70) of the mouthpiece forms a certain angle with the longitudinal axis (60) of the intake section, with the vertex of the angle being the swivel joint (80) connecting the mouthpiece (40) and the mixing section (30). The latch mechanism (296) for the cover (290) of the mixing section can accomplish this, by any of several mechanical means known to those of ordinary skill in the art. In the simplest embodiment, a catchment (not shown) in the cover (290) for the mixing chamber would be engaged by a slip ring (not shown) on the mixing section which was only a certain number of degrees of a circle.

When the mouthpiece (40) were rotated enough relative to the intake section (20), the slip ring (not shown) would no longer engage the catchment (not shown). In one embodiment, the user could open the cover (290) when the angle were between approximately ninety and one-hundred and eighty degrees.

Figure 7:
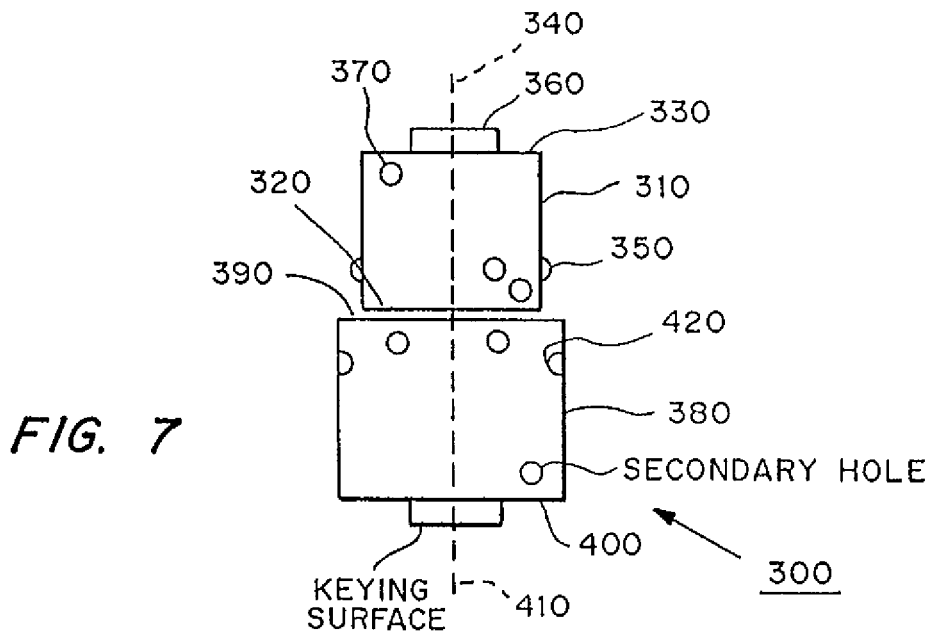
FIG. 7 is a schematic view of a capsule to hold medicament.
Figure 14:
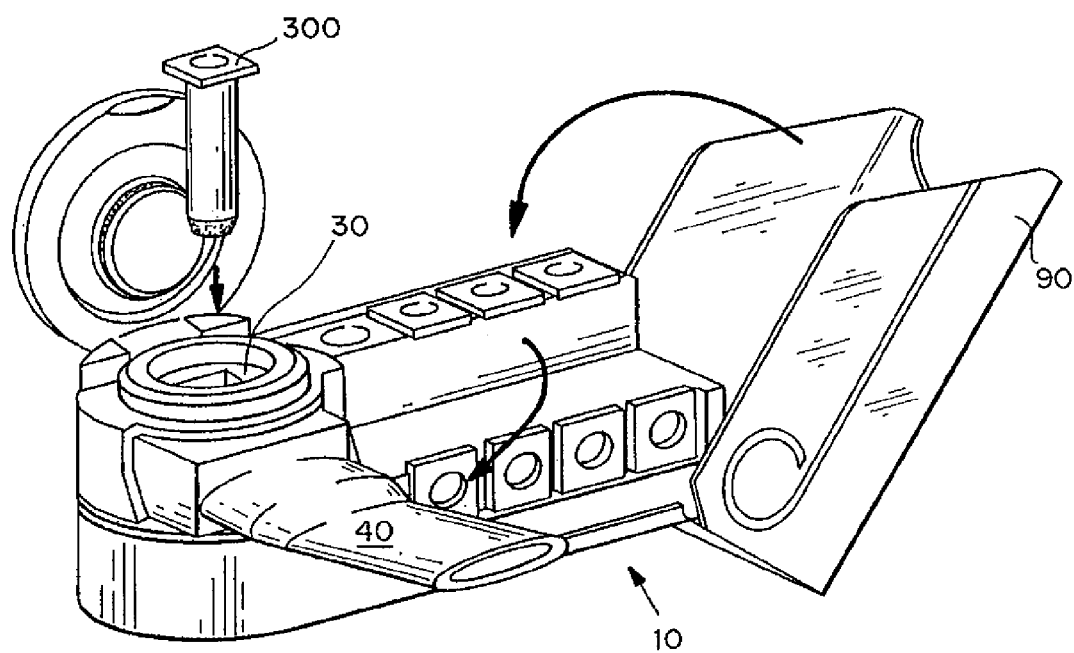
Figure 15:
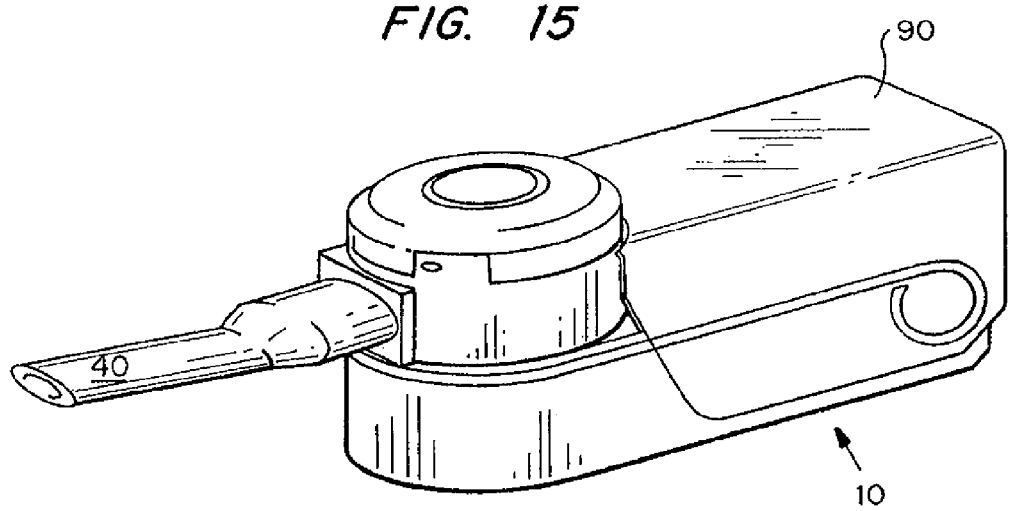
Figure 16:
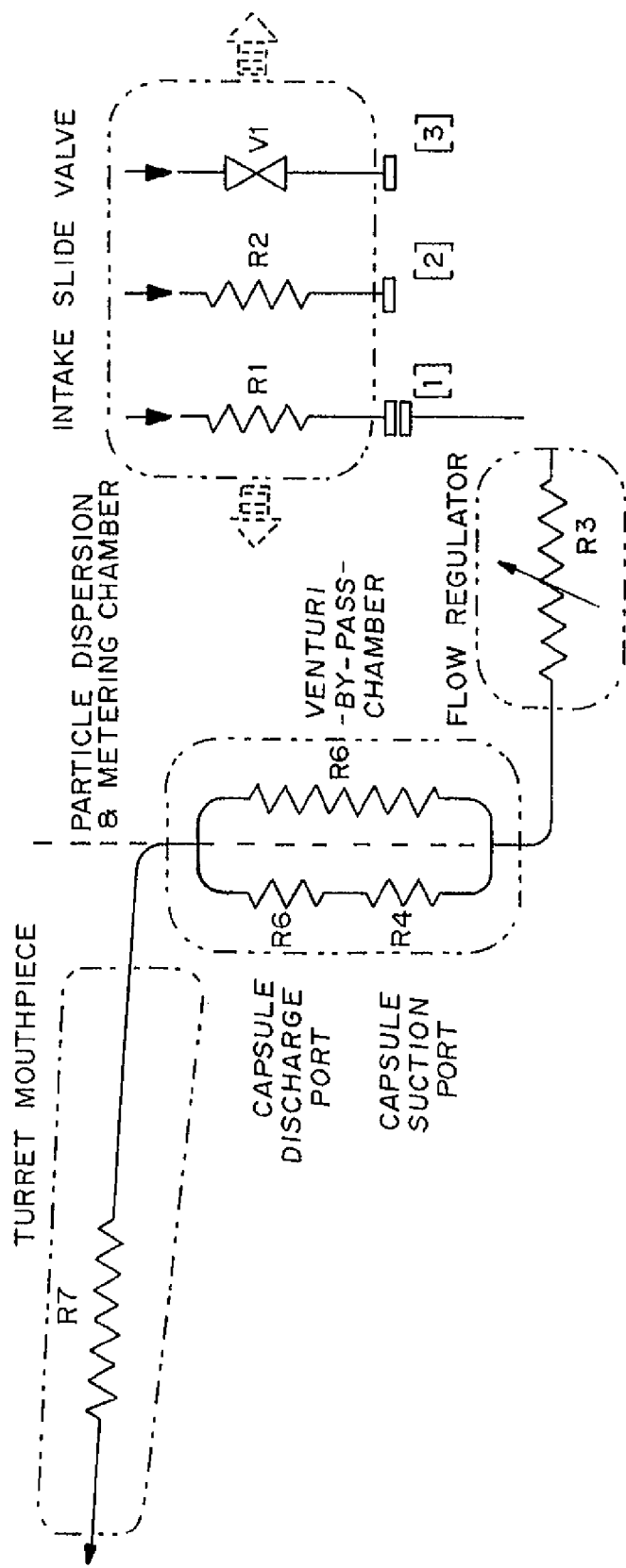
FIG. 16 is a view of a pneumatic circuit, where air flows (fluid flows) are represented by their electrical equivalents.
Figure 17:
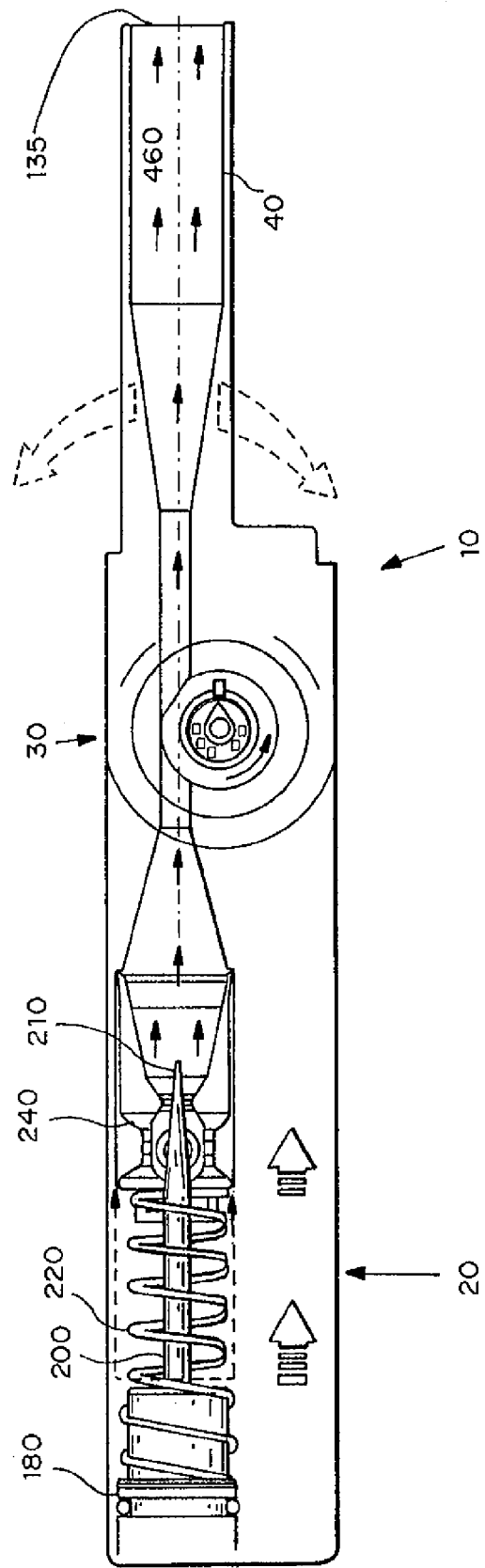
FIG. 17 is a schematic view of the dry particle inhaler.

FIG. 7 shows a medicament capsule (300) for use with an inhaler, be it a dry powder inhaler (10), or a liquid mist inhaler. The capsule (300) has two halves which fit together, here styled a first tube (310) and a second tube (380). Each tube has an open end (320,390), and a closed end (330,400). Each tube also has a long axis (340,410). In addition, each tube has a number of secondary holes (370,440). The first tube (310) fits inside the second tube (380) snugly. A protrusion (350) on the outer surface of the first tube (310) can slide past a corresponding protrusion (420) on the inner surface of the second tube (380). This locks the first tube (310) to the second tube (380). Therefore the first tube (310) and the second tube (380) have both an unlocked and a locked position. In the unlocked position, at least one secondary hole (370) in the first tube aligns with at least one secondary hole (440) in the second tube. This permits introduction of a medicament (not shown) into the capsule through the aligned secondary holes (370,440).

The first tube (310) may then be locked to the second tube (380). When a user (not shown) is ready to use a capsule (300), he simply places it in the holder (260) in the mixing section (30), and closes the cover (290). When the holder (260) rotates the first tube (310) around its long axis (340) relative to the second tube (380) and its long axis (410) (the axes are now coincident), that causes at least two secondary holes (370) in the first tube to align with at least two secondary holes (440) in the second tube. Air can now pass in, through, and out of the capsule (300), releasing the medicament contained therein. In one embodiment of the inhaler, the capsule (300) might open when the angle between the longitudinal axis (70) of the mouthpiece section, the vertex of the swivel joint (80), and the longitudinal axis (70) of the mouthpiece section were between one hundred and seventy and one-hundred and eighty degrees. This rotation of the mouthpiece (40) relative to the intake section (20) would cause a corresponding rotation of the first tube (310) about its long axis (340) relative to the second tube (380) and its long axis (410).

In one embodiment of the invention, several protrusions on the surfaces of the first tube or the second tube might provide a variety of locking positions. Similarly, a variety of secondary holes in the first and second tubes might provide a variety of rotational positions aligning or not aligning secondary holes on the first and second tubes.

The capsules described herein permit the introduction of liquid or gel medicament which can be dried in the capsule, creating a powder. This permits the accurate production of very small amounts of powdered medicament in a capsule, since it can be formed from a larger volume of accurately metered liquid or gel medicament. This permits very accurate microdosing. In addition, chemical reactions and drug mixtures may be made directly in the capsules described herein, then the resulting formulation dried.

In one embodiment of the capsule (300), one or more of the secondary holes (370,440) used to admit air to the capsule is oval-shaped (elliptical). In one embodiment of the invention, the ratio of the long axis of the ellipse to the shorter axis may be between 1:1 and 3:1, and may be 2:1.

This ratio may be called a vertical aspect ratio. In one embodiment of the invention, the intersection of the surface defining one or more of the secondary holes (370,440) and the surface defining the interior of the capsule (300) meet in a chamfered, or beveled, edge. This chamfered edge creates a vortex when air flows through the secondary holes (370,440).

Each capsule (300) also has a keying surface (or fastening mechanism) on the closed end (330) of the first tube and the closed end (400) of the second tube comprising the capsule.

The keying surface (360) on the first tube may be different from the keying surface (430) on the second tube.

That permits easy tactile and visual identification of the orientation of the capsule. It also permits a system where each drug formulation in a capsule (300) corresponds to a dry particle inhaler (10), so users cannot mix up drugs. In one embodiment of the invention, the keying surface (360) of the first tube mates with a keying surface (430) of a different second tube, or the mechanical fasteners (250) of the storage section (470). This permits easy storage of the capsules (300) in the storage section (470).

FIG. 18 shows a medicament capsule (300), with a keying surface (360) on the first tube and a keying surface (430) on the second tube. It also shows a cutaway view of the mixing section (30) and the air flow entrance (292) to the mixing section and the air flow exit (294) to the mixing section.

A spiral shape (280) is given to the interior walls (298) of the mixing section, to impart a cyclonic flow to air passing through. The air flow entrance (292) and air flow exit (294) in this embodiment are tangential to the imaginary tube we might call the mixing section interior (291). That is to say, if a radius were drawn perpendicular to the long axis of the tube, and a tangent line were drawn to the circle perpendicular to the radius, the air flow would exit the mixing section along that tangent line. The tangential air flow exit (294) increases the velocity of the air flow, and thus helps disperse the medicament particles. As can be seen from FIG. 18, the mixing section interior (291) is sized to accommodate a medicament capsule (300). Keying mechanisms (360,430) are shaped to mate with holder (260) in the mixing section. Capsules according to the present invention may have a number of shapes, including ovoid and rectangular shapes. A variety of shapes of protrusions and slots may also be employed as keying surfaces. For instance, a keying surface might be a rectangular block, and a capsule holder might have a rectangular orifice. Alternatively, a keying surface might be triangular, hexagonal, Z-shaped, C-shaped, etc., and the holder would have the correspondingly shaped aperture.

FIG. 18 also shows one embodiment of the capsule (300) where a cone (375) is located in the interior of the first tube, and a cone (445) is located in the interior of the second tube. These cones (375,445) cause the air flow within the capsule to be cyclonic, aiding in mixing the medicament particles with the air. A cone is shown herein, but other cyclone-creating structures are contemplated by the present invention.

FIG. 8 shows the mouthpiece (40) of the dry particle inhaler (10).

It has a protrusion (130) on its surface to contact the lips of a user (not shown). This helps the user place the mouthpiece correctly in his mouth.

The mouthpiece (40) also includes a tongue depressor (120), which may have a bulbous shape. The mouthpiece (40) is long enough that it fits approximately midway into the user's mouth (not shown). This permits greater delivery of medicament to the lungs, and less delivery to the oral cavity. The mouthpiece (40) has a particular aspect ratio of its inner channel (50) (see FIG. 17). This slows the air passing through the channel so that the air borne particulates do not end up striking the back of the user's throat.

However, the air is not slowed so much that the particulates settle out of the air flow.

FIG. 9, FIG. 10, and FIG. 11 show one specific embodiment of the dry particle inhaler (10). In FIG. 9, the cover (90) of the mouthpiece is closed, and several capsule (300) are in the storage section (470). In FIG. 10, the mouthpiece (40) has been rotated relative to the intake section (20). The longitudinal axis (60) [not shown] of the intake section here makes an approximately ninety degree angle with the longitudinal axis (70) of the mouthpiece section. This permits the cover (290) for the mixing section to be opened. A medicament capsule (300) taken from the storage section (470) is about to be inserted into the mixing section (30). In FIG. 11, the mouthpiece (40) has been rotated to a fully extended position, the cover (290) for the mixing section has been closed, and the dry particle inhaler 910) is ready for use. In one embodiment of the dry particle inhaler (10), when the dry particle inhaler is in the closed position (FIG. 9), the interior of the intake section (20) would be isolated from the outside air, but the mouthpiece (40) interior and the mixing section interior (291) would not be, permitting them to dry out after being exposed to the humid breath of a user.

FIG. 12, FIG. 13, FIG. 14, and FIG. 15 show a temporal sequence where a capsule (300) of medicament is loaded into the mixing section (30) of a dry particle inhaler (10), and the mouthpiece (40) is extended for use. The dry particle inhaler (10) described herein can also be used for nasal delivery of medicaments. A small tube (not shown) can be fitted to the end of the mouthpiece (40), and the other end of the tube inserted into the nostril. Alternatively, the mouthpiece (40) may be replaced by a nosepiece (not shown), whose free end is sized to be inserted into a nostril of a user. In another embodiment, a device such as a bellows or a syringe is used to force air through the dry particle inhaler (10) into a nosepiece inserted into the nostril of a user (not shown).

FIG. 16 shows the fluid (air) flow of the dry particle inhaler (10) modeled as the equivalent electrical circuit. This is styled a "pneumatic resistance circuit".

FIG. 17 shows a schematic view of the dry particle inhaler (10). The air passage (50) through the dry particle inhaler widens as it goes through the mouthpiece (40) along the direction of the air flow (460). The opening (135) of the mouthpiece to be inserted into the mouth of the user may be roughly ellipsoid, or oval, and thus have a major axis and a minor axis. The ratio of these two may be called the horizontal aspect ratio. In one embodiment of the invention, the horizontal aspect ratio is between 2:1 and 4:1. In one embodiment of the dry particle inhaler (10), the horizontal aspect ratio is 3:1. Shaping the opening (135) in this manner keeps the drug particles collimated, maintains the optimal velocity of the particles in the air stream, and is oriented to the natural horizontal aspect ratio of the oropharyngeal region of the mouth. In one embodiment of the invention, the outline of the opening (135) resembles a bean.

The dry particle inhaler described herein may be used with medicament particles of low, medium, and high shear forces.

The dry particle inhaler and capsules described herein may be made with a variety of suitable materials known to those skilled in the art, such as metal, glass, rubber, and plastic.

While the invention has been described with reference to particular embodiments, those skilled in the art will be able to make various modifications without departing from the spirit and scope thereof.

We claim:

1. A capsule for a dry powder inhaler comprising:

a first keying surface on a top half of the capsule and a second keying surface on a bottom half of the capsule, wherein the top half and bottom half comprise an outer surface and one or more protrusions to lock and/or unlock the capsule;

an air input hole, and a tangential airflow exit hole;

said capsule having a substantially cylindrical interior shape when the top half and bottom half of the capsule are fitted together;

wherein in an unlocked capsule a hole in the surface of the top half aligns with a hole in the bottom half to direct airflow into the capsule.

2. The capsule according to claim 1 wherein the first keying surface and the second keying surface are the same.

3. The capsule according to claim 1 wherein the first keying surface and the second keying surface are different.

4. The capsule according to claim 1 wherein the second keying surface compliments a movable keying surface on an inhaler.

5. The capsule according to claim 4 wherein the movable keying surface is associated with a joint.

6. The capsule according to claim 1 wherein the air input has a ratio of long axis to short axis of between about 2:1 and about 3:1.

7. The capsule according to claim 6 wherein the ratio is about 3:1.

8. The capsule according to claim 1 wherein the tangential airflow exit leads directly into a mouthpiece of an inhaler.

9. The capsule according to claim 1 wherein the second keying surface is rectangular.

10. The capsule according to claim 1 wherein the first keying surface is triangular.

11. The capsule according to claim 1 further comprising a medicament.

12. The capsule according to claim 11 wherein the medicament is a gel, liquid or dry powder.

13. The capsule according to claim 12 wherein the medicament is a dry powder.

* * * * *